(12) United States Patent
Barrall

(10) Patent No.: US 9,119,725 B2
(45) Date of Patent: Sep. 1, 2015

(54) EXPANDABLE VERTEBRAL BODY REPLACEMENT SYSTEM AND METHOD

(75) Inventor: Ben Barrall, Conshohocken, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 246 days.

(21) Appl. No.: 13/141,235

(22) PCT Filed: Dec. 1, 2009

(86) PCT No.: PCT/US2009/006316
§ 371 (c)(1),
(2), (4) Date: Jun. 21, 2011

(87) PCT Pub. No.: WO2010/074700
PCT Pub. Date: Jul. 1, 2010

(65) Prior Publication Data
US 2011/0257750 A1    Oct. 20, 2011

Related U.S. Application Data

(60) Provisional application No. 61/139,937, filed on Dec. 22, 2008.

(51) Int. Cl.
*A61F 2/44* (2006.01)
*A61F 2/46* (2006.01)
*A61F 2/30* (2006.01)

(52) U.S. Cl.
CPC . *A61F 2/44* (2013.01); *A61F 2/442* (2013.01); *A61F 2/4611* (2013.01); *A61F 2/4455* (2013.01);
(Continued)

(58) Field of Classification Search
CPC ............ A61F 2/44–2/447; A61F 2/4611;
A61F 2/4455; A61F 2/4425; A61F 2002/30579; A61F 2002/30604; A61F 2002/4627; A61F 2002/30601; A61F 2002/0025
USPC .............. 606/279, 90, 105; 623/17.11–17.16; 187/211; 254/10 C, 15, 16, 115
See application file for complete search history.

(56) References Cited

U.S. PATENT DOCUMENTS 5,782,832 A   7/1998  Larsen et al.
6,126,689 A * 10/2000 Brett ......................... 623/17.16
(Continued)

FOREIGN PATENT DOCUMENTS

JP    2004-530527    10/2004
JP    2007-515197    6/2007
(Continued)

*Primary Examiner* — Eduardo C Robert
*Assistant Examiner* — Michelle C Eckman
(74) *Attorney, Agent, or Firm* — Baker & Hostetler LLP

(57) ABSTRACT

Vertebral body replacement apparatuses, systems, and methods are provided. In various examples, an implantable device is configured to be inserted between a first vertebral body and a second vertebral body. The implantable device includes a first endplate configured to contact a superior endplate of the first vertebral body. A central member is pivotably coupled to the first endplate. A second endplate is configured to contact an inferior endplate of the second vertebral body. The implantable device includes a first insertion configuration and a second load-bearing configuration. The first insertion configuration includes the central member at a first angular position with respect to the first endplate. The second load-bearing configuration includes the central member at a second angular position with respect to the first endplate and the second endplate in a load-bearing position.

38 Claims, 19 Drawing Sheets

(52) U.S. Cl.
CPC ... *A61F 2002/305* (2013.01); *A61F 2002/3052* (2013.01); *A61F 2002/3055* (2013.01); *A61F 2002/30387* (2013.01); *A61F 2002/30405* (2013.01); *A61F 2002/30471* (2013.01); *A61F 2002/30522* (2013.01); *A61F 2002/30551* (2013.01); *A61F 2002/30579* (2013.01); *A61F 2002/30601* (2013.01); *A61F 2002/30632* (2013.01); *A61F 2002/30677* (2013.01); *A61F 2002/30904* (2013.01); *A61F 2002/4415* (2013.01); *A61F 2220/0025* (2013.01); *A61F 2220/0091* (2013.01); *A61F 2310/00017* (2013.01); *A61F 2310/00023* (2013.01); *A61F 2310/0097* (2013.01)

(56) References Cited

U.S. PATENT DOCUMENTS

| | | | |
|---|---|---|---|
| 6,190,414 B1* | 2/2001 | Young et al. | 623/17.15 |
| 6,395,031 B1* | 5/2002 | Foley et al. | 623/17.11 |
| 6,454,806 B1* | 9/2002 | Cohen et al. | 623/17.15 |
| 6,730,088 B2* | 5/2004 | Yeh | 606/247 |
| 2005/0060036 A1 | 3/2005 | Schultz et al. | |
| 2005/0261683 A1* | 11/2005 | Veldhuizen et al. | 606/61 |
| 2006/0030943 A1* | 2/2006 | Peterman | 623/17.11 |
| 2006/0085070 A1* | 4/2006 | Kim | 623/17.11 |
| 2006/0142858 A1* | 6/2006 | Colleran et al. | 623/17.11 |
| 2006/0224241 A1* | 10/2006 | Butler et al. | 623/17.15 |
| 2006/0235423 A1* | 10/2006 | Cantu | 606/90 |
| 2006/0293755 A1 | 12/2006 | Lindner et al. | |
| 2007/0191958 A1 | 8/2007 | Abdou | |
| 2009/0024217 A1* | 1/2009 | Levy et al. | 623/17.16 |
| 2009/0076607 A1* | 3/2009 | Aalsma et al. | 623/17.16 |
| 2009/0125062 A1* | 5/2009 | Arnin | 606/246 |
| 2009/0299478 A1* | 12/2009 | Carls et al. | 623/17.16 |
| 2010/0137987 A1* | 6/2010 | Diao et al. | 623/17.15 |
| 2010/0145456 A1* | 6/2010 | Simpson et al. | 623/17.16 |
| 2010/0262247 A1* | 10/2010 | Arnin | 623/17.16 |
| 2010/0331983 A1* | 12/2010 | Sankaran | 623/17.11 |
| 2011/0015638 A1* | 1/2011 | Pischl et al. | 606/90 |
| 2011/0178600 A1* | 7/2011 | Moskowitz et al. | 623/17.16 |
| 2012/0179258 A1* | 7/2012 | Glazer et al. | 623/17.16 |

FOREIGN PATENT DOCUMENTS

| | | |
|---|---|---|
| JP | 2008-501462 | 1/2008 |
| JP | 2008-502374 | 1/2008 |
| JP | 2008-512218 | 4/2008 |
| WO | WO 2007/140382 A2 | 12/2007 |
| WO | WO 2010/074700 A1 | 7/2010 |

\* cited by examiner

EXPANDABLE VERTEBRAL BODY
REPLACEMENT SYSTEM AND METHOD

CROSS-REFERENCE TO RELATED APPLICATIONS

This application is the National Stage of International Application No. PCT/US2009/006316, filed Dec. 1, 2009, which claims the benefit of U.S. Provisional Application No. 61/139,937, filed Dec. 22, 2008, the disclosures of which are incorporated herein by reference in their entireties for all purposes.

TECHNICAL FIELD

This patent document pertains generally to orthopedics. More particularly, but not by way of limitation, this patent document pertains to a system, apparatus, and method for vertebral body replacement for the spine using low insertion-profile implants.

BACKGROUND

Vertebral body replacement devices, or corpectomy implants, are indicated to provide anterior column support following a corpectomy, vertebrectomy, or spondylectomy as a result of trauma to the spine, removal of tumor material from the spinal column, or to correct spinal deformity. Surgeons may utilize a number of different devices to provide this anterior column support, including structural bone struts made from auto- or allograft tissue, structural titanium mesh cages, and expandable titanium devices. The majority of these devices are designed to be introduced through a direct anterior, anterolateral, or direct lateral approach channel that is perpendicular to the spinal column, with the implant itself oriented parallel with the axis of the spine. However, in cases where it is desirable to address the patient's pathology from a posterior or posterolateral approach, the patient's neurological structures, including the spinal cord, cauda equina, and exiting nerve roots, limit the available access to the corpectomy defect, limiting the use of many of the currently known devices, or forcing the surgeon to use an implant size or configuration that is less than optimal.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

Figure 1:
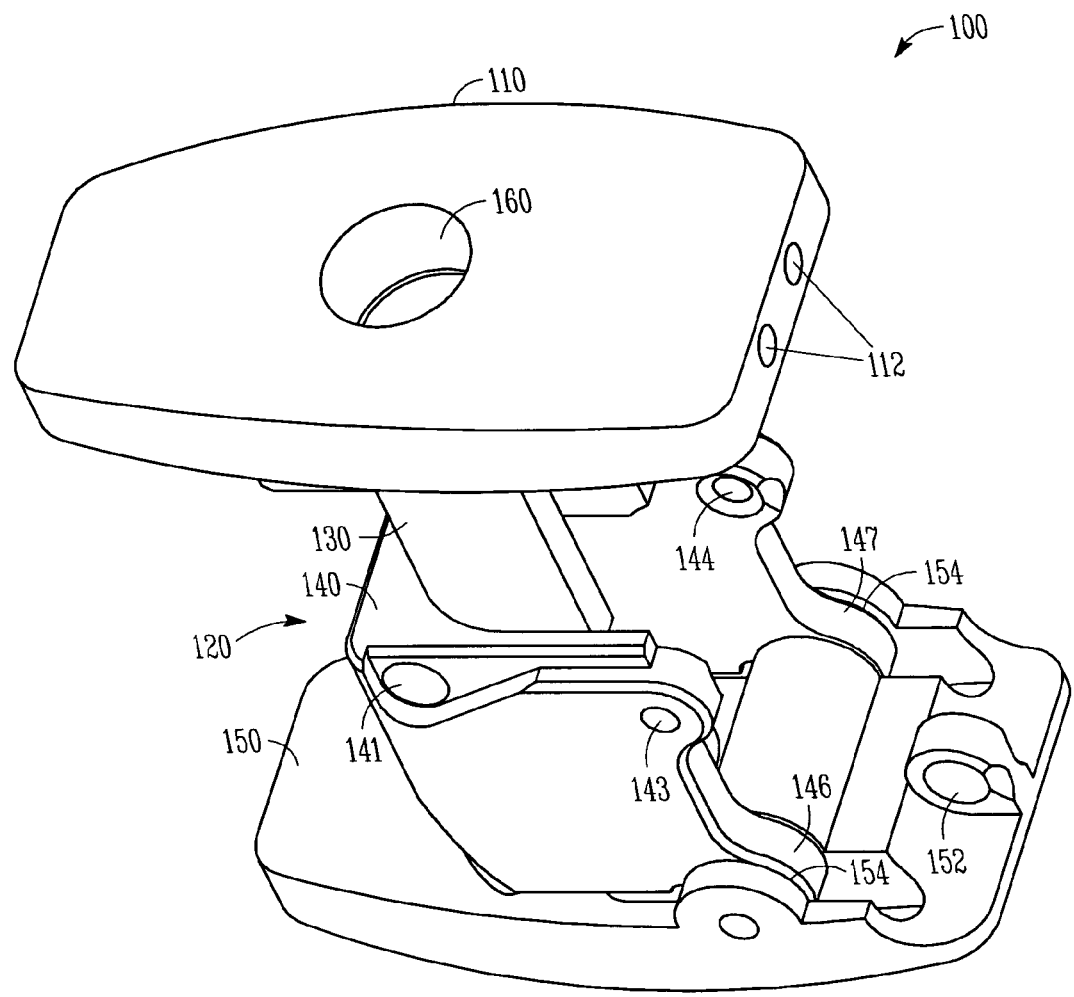
FIG. 1 illustrates a front perspective view of a low insertion profile vertebral body replacement implant in accordance with an example of the present invention in an expanded, load-bearing configuration.

Certain terminology is used in the following description for convenience only and is not limiting. The words "right", "left", "lower", and "upper" designate directions in the drawings to which reference is made. The words "inwardly" or "distally" and "outwardly" or "proximally" refer to directions toward and away from, respectively, the geometric center of the low insertion profile vertebral body replacement implant, related instruments and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

The present inventor has recognized, among other things, that limited access to a corpectomy defect from a posterior or posterolateral approach presents problems during vertebral body replacement surgical procedures. The present inventor has further recognized that there exists an unmet need for a corpectomy implant configured for posterior or posterolateral approach that can be introduced in a minimally invasive, tissue-sparing manner, and provide stable structural support.

This patent document describes, among other things, apparatuses, systems, and methods for vertebral body replacement for the spine using low insertion-profile implants. In various examples, an implantable device is configured to be inserted between a first vertebral body and a second vertebral body. The implantable device includes a first endplate configured to contact a superior endplate of the first vertebral body. A central member is pivotably coupled to the first endplate. A second endplate is configured to contact an inferior endplate of the second vertebral body. The implantable device includes a first insertion configuration and a second load-bearing configuration. The first insertion configuration includes the central member at a first angular position with respect to the first endplate. The second load-bearing configuration includes the central member at a second angular position with respect to the first endplate and the central member engaged with the second endplate.

In Example 1, a system includes an implantable device configured to be inserted between a first vertebral body and a second vertebral body. The implantable device includes a first endplate having a superior surface and an inferior surface. The inferior surface is configured to contact a superior endplate of the first vertebral body. A central member is pivotably coupled to the first endplate. The central member includes a first coupling feature. A second endplate has a superior surface and an inferior surface. The superior surface is configured to contact an inferior endplate of the second vertebral body. The second endplate includes a second coupling feature configured to engage with the first coupling feature of the central member. The implantable device includes a first insertion configuration and a second load-bearing configuration. An insertion instrument is removably couplable to the implantable device. The insertion instrument is configured to advance the implantable device in the first insertion configuration in between the superior endplate of the first vertebral body and the inferior endplate of the second vertebral body. The insertion instrument is actuatable to place the implantable device in the second load-bearing configuration with the central member pivoted with respect to the first endplate and the second endplate moved with respect to the central column into a load-bearing position with the first coupling feature of the central member engaged with the second coupling feature of the second endplate.

In Example 2, the system of Example 1 optionally is configured such that the central member is pivotable through substantially ninety degrees with respect to the first endplate.

In Example 3, the system of one or more of Examples 1-2 optionally is configured such that the second coupling feature is configured to slidingly engage with the first coupling feature of the central member.

In Example 4, the system of one or more of Examples 1-3 optionally is configured such that the second coupling feature of the second endplate is pivotably engaged with the first coupling feature of the central member.

In Example 5, the system of one or more of Examples 1-4 optionally is configured such that a height of the implantable device in the first insertion configuration is less than a height of the implantable device in the second load-bearing configuration.

In Example 6, the system of one or more of Examples 1-5 optionally is configured such that the central member is pivotably coupled proximate a proximal side of the superior surface of the first endplate.

In Example 7, the system of one or more of Examples 1-6 optionally is configured such that the central member includes an inner strut member and an outer strut member. The inner strut member is telescopically movable with respect to the outer strut member.

In Example 8, the system of Example 7 optionally comprises an expansion mechanism configured to telescopically move the inner strut member with respect to the outer strut member.

In Example 9, the system of Example 8 optionally is configured such that the expansion mechanism includes a rack and pinion.

In Example 10, the system of one or more of Examples 1-9 optionally is configured such that the insertion instrument is couplable to the second endplate. The insertion instrument is configured to slidingly advance the second endplate into engagement with the first coupling feature of the central member.

In Example 11, the system of one or more of Examples 1-10 optionally is configured such that the central member includes at least first and second pivoting segments. The first pivoting segment is pivotable with respect to the first endplate. The second pivoting segment is pivotable with respect to the first pivoting segment.

In Example 12, the system of one or more of Examples 1-11 optionally is configured such that the central member is lockable in a pivoted position. The central member is in the pivoted position with the implantable device in the second load-bearing configuration.

In Example 13, the system of one or more of Examples 1-12 optionally is configured such that the insertion instrument includes a first sliding arm and a second sliding arm. The second sliding arm is configured to slide to pivot the central member with respect to the first endplate. The first sliding arm is configured to slide to engage the first coupling feature of the central member with the second coupling feature of the second endplate.

In Example 14, the system of Example 13 optionally is configured such that the insertion instrument includes a third sliding arm. The second sliding arm is slidable with respect to the third sliding arm to pivot the central member with respect to the first endplate. The first sliding arm is slidable with respect to the second sliding arm to engage the first coupling feature of the central member with the second coupling feature of the second endplate.

In Example 15, an implantable device is configured to be inserted between a first vertebral body and a second vertebral body. The implantable device comprises a first endplate having a superior surface and an inferior surface. The inferior surface is configured to contact a superior endplate of the first vertebral body. A central member is pivotably coupled to the first endplate. The central member includes a first coupling feature. A second endplate has a superior surface and an inferior surface. The superior surface is configured to contact an inferior endplate of the second vertebral body. The second endplate includes a second coupling feature configured to engage with the first coupling feature of the central member. The implantable device includes a first insertion configuration and a second load-bearing configuration. The first insertion configuration includes the central member at a first angular position with respect to the first endplate. The second load-bearing configuration includes the central member at a second angular position with respect to the first endplate and the second endplate in a load-bearing position with the first coupling feature of the central member engaged with the second coupling feature of the second endplate.

In Example 16, the implantable device of Example 15 optionally is configured such that the central member is pivotable from the first angular position through substantially ninety degrees with respect to the first endplate to the second angular position.

In Example 17, the implantable device of one or more of Examples 15-16 optionally is configured such that the second coupling feature of the second endplate is configured to slidingly engage with the first coupling feature of the central member.

In Example 18, the implantable device of one or more of Examples 15-17 optionally is configured such that the second coupling feature of the second endplate is pivotably engaged with the first coupling feature of the central member.

In Example 19, the implantable device of one or more of Examples 15-18 optionally is configured such that a height of the implantable device in the first insertion configuration is less than a height of the implantable device in the second load-bearing configuration.

In Example 20, the implantable device of one or more of Examples 15-19 optionally is configured such that the central member includes an inner strut member and an outer strut member. The inner strut member is telescopically movable with respect to the outer strut member.

In Example 21, the implantable device of one or more of Examples 15-20 optionally comprises an expansion mechanism configured to telescopically move the inner strut member with respect to the outer strut member.

In Example 22, the implantable device of one or more of Examples 15-21 optionally is configured such that the central member includes at least first and second pivoting segments. The first pivoting segment is pivotable with respect to the first endplate. The second pivoting segment is pivotable with respect to the first pivoting segment.

In Example 23, the implantable device of one or more of Examples 15-22 optionally is configured such that the central member is lockable in the second angular position. The central member is in the second angular position with the implantable device in the second load-bearing configuration.

In Example 24, the implantable device of one or more of Examples 15-23 optionally is configured such that the implantable device is configured to detachably engage with an insertion instrument. The insertion instrument is configured to advance the implantable device in the first insertion configuration in between the superior endplate of the first vertebral body and the inferior endplate of the second vertebral body. The insertion instrument is actuatable to place the implantable device in the second load-bearing configuration.

In Example 25, a method comprises placing an implantable device, in a first insertion configuration, between a first vertebral body and a second vertebral body using an insertion device. The implantable device is removably coupled to the insertion device. A central member of the implantable device is pivoted from a first angular position with respect to a first endplate of the implantable device to a second angular position with respect to the first endplate. A second endplate of the implantable device is moved into a load-bearing position at an end of the central member to place the implantable device in a second load-bearing configuration.

In Example 26, the method of Example 25 optionally is configured such that pivoting the central member includes pivoting the central member substantially ninety degrees.

In Example 27, the method of one or more of Examples 25-26 optionally is configured such that pivoting the central member includes actuating the insertion instrument to pivot the central member.

In Example 28, the method of Example 27 optionally is configured such that actuating the insertion instrument includes sliding one sliding arm of the insertion instrument with respect to another sliding arm of the insertion instrument.

In Example 29, the method of one or more of Examples 25-28 optionally is configured such that moving the second endplate includes actuating the insertion instrument to move the second endplate into engagement with the central member.

In Example 30, the method of Example 29 optionally is configured such that actuating the insertion instrument includes sliding one sliding arm of the insertion instrument with respect to another sliding arm of the insertion instrument.

In Example 31, the method of one or more of Examples 25-30 optionally is configured such that moving the second endplate includes pivoting the second endplate with respect to the central member.

In Example 32, the method of one or more of Examples 25-31 optionally comprises removing the insertion instrument from engagement with the implantable device.

In Example 33, the method of one or more of Examples 25-32 optionally is configured such that pivoting the central member includes locking the central member in the second angular position.

In Example 34, the method of one or more of Examples 25-33 optionally comprises expanding the implantable device to increase a height of the implantable device.

In Example 35, the method of Example 34 optionally is configured such that expanding the implantable device includes actuating an expansion mechanism to telescopically move an inner strut member of the central member with an outer strut member of the central member.

Referring to FIGS. 1-15, in an example, a low insertion-profile vertebral body replacement (VBR) implant 100 and an associated insertion instrument 200 are provided. The implant 100 includes a superior end, an inferior end, and a longitudinal axis therebetween. The implant 100 further includes a proximal end engageable with the instrument 200 and a distal end opposite the proximal end. The implant 100 includes a superior endplate 110 that is couplable with a central column 120 and the central column 120 further includes an inner strut member 130 and an outer strut member 140. In an example, the inner strut member 130 is disposed in the interior of the outer strut member 140. The superior endplate 110 is, in an example, slidably lockable to the top surface of the inner strut member 130 via the inclusion of, for example, a dovetail and accommodating groove. The superior endplate 110 further includes a proximally disposed superior endplate instrument engagement feature 112. In another example, the superior endplate 110 is pivotably coupled to the central column 120 such that the superior endplate 110 is pivotable into place during insertion of the implant 100. In a further example, the superior endplate 110 includes a locking or engaging feature to maintain the superior endplate 110 in place on the central column 120 once the superior endplate 110 is pivoted into place.

The inner strut member 130 and the outer strut member 140 are telescopically expandable in height with respect to one another to provide a low insertion height/profile and permit expansion into a final expanded configuration between vertebral bodies. In various examples, the inner strut member 130 is translatable with respect to the outer strut member 140 to thereby provide height expansion to the central column 120 via the inclusion of an expansion mechanism 122. In various examples, the expansion mechanism 122 includes a ratcheting expansion mechanism, a threaded expansion mechanism, a rack and pinion expansion mechanism, a stacking shim expansion mechanism, or other expansion mechanism. In the example shown in FIG. 14, the expansion mechanism 122 includes a pinion 124 operatively coupled to and selectively actuated using the insertion instrument 200. The pinion 124 is positionable in engagement with a rack 126 within the inner strut member 130. Actuation of the pinion 124 translates the rack 126 with respect to the pinion 124 and, in turn, telescopically translate the inner strut member 130 with respect to the outer strut member 140. In this way, the expansion mechanism 122 is used to selectively expand the height of the central column 120. In some examples, the expansion mechanism 122 includes a pawl or other feature to inhibit reverse movement of the inner strut member 130 with respect to the outer strut member 140 to inhibit the expanded central column 120 from retracting.

The inner strut member 130 and the outer strut member 140 may be open ended, such that each assumes a C-shape in cross section. Alternatively, the inner strut member 130 and the outer strut member 140 may take-on hollow cylindrical or other tubular forms. In an example, an inferior endplate 150 is couplable to the inferior proximal end of the outer strut member 140 via a claw-like first outer strut hinge coupling 146 and a claw-like second outer strut hinge coupling 147 that combine with a pin-like feature or a pair of pin-like features (not shown) on the inferior endplate 150 to form an inferior endplate hinge 154 that enables the central column 120 to rotate with respect to the inferior endplate 150 between an insertion configuration and a load bearing configuration. In an example, the central column 120 rotates through approximately ninety degrees with respect to the inferior endplate 150 between the insertion configuration and the load bearing configuration. In other examples, the central column 120 rotates through greater than or less than ninety degrees with respect to the inferior endplate 150 between the insertion configuration and the load bearing configuration, depending upon various factors including, for instance, the location for the implant 100 relative to the access channel, or the angular orientation of the final configuration of the implant 100 with respect to the access channel. The height of the implant 100 in the load-bearing configuration is greater than the height of the implant 100 in the insertion configuration. A variety of other mechanisms can be utilized to form the inferior endplate hinge 154 in addition to the claw-like first and second outer strut hinge couplings 146, 147 and the pin-feature on the inferior endplate 150. In an example, the central column can include two or more segments pivotably coupled to one another, such that a first segment is pivotably coupled to the inferior endplate 150 and a second segment is pivotably coupled to the first segment and so on. In this way, the first segment can be pivoted into place with respect to the inferior endplate 150 and then each additional segment can be pivoted into place in series thereafter to erect the central column. In an example, the length of each segment of the central column can be selected and determined by the amount of access space available. In various examples, the two or more segments are each lockable into place.

In an example, the outer strut member 140 includes a first outer strut instrument engagement feature 141 and a second outer strut instrument engagement feature (not shown) disposed on opposite distal superior ends of the outer strut member 140 in its load-bearing configuration. The outer strut member 140 further includes a third outer strut instrument engagement feature 143 and a fourth outer strut instrument engagement feature 144 disposed on opposite proximal superior ends of the outer strut member 140 in its load-bearing configuration. The inferior distal surface of the outer strut member 140 further includes an optional first snap lock feature 145 that is configured to mate with a corresponding optional second snap-lock feature 155 on the superior surface of the inferior endplate 150 to retain the central column 120 securely with respect to the inferior endplate 150 in the load bearing configuration. The inferior endplate 150 further includes a proximally disposed inferior endplate engagement feature 152.

In an example, the superior surface of the superior endplate 110 is configured to contact the inferior endplate of a superior vertebral body and the inferior surface of the inferior endplate 150 is configured to contact the superior endplate of an inferior vertebral body. The superior and inferior endplates 110, 150 may include teeth, serrations, ridges, or other anti-repulsion features to secure the endplates 110, 150 to the vertebral bodies in the implanted position. The superior and inferior endplates 110, 150 may be formed in a variety of modular geometries, including circular, ovular, kidney bean-shaped, etc., to conform ideally to the endplates of the adjacent vertebral bodies. The superior and inferior endplates 110, 150 may further be flat, tapered, concave, or convex to further accommodate the anatomy of the adjacent vertebral endplates. The superior and inferior endplates 110, 150 may further include brachytherapy seeds for treating tumors or may be coated or surface treated with beneficial agents. The superior and inferior endplates 110, 150 may formed from rigid biocompatible material, such as titanium, stainless steel, or polymers such as PEEK. Alternately, the superior and inferior endplates 110, 150 can be formed from semi-rigid material to enable the superior and inferior endplates 110, 150 to conform to the anatomy of the adjacent vertebral endplates via a force-fit in the implanted position.

Disposed through the center of the implant 100 along the longitudinal axis is an optional axial bore 160 configured to house graft material or allow boney through-growth to enable fusion to occur through the implant 100.

In various examples, the insertion instrument 200 includes a proximal end and a distal end and a longitudinal axis extending therebetween. In some examples, the instrument 200 includes a first sliding arm 210, a second sliding arm 220, and a third sliding arm 230, wherein the first and second sliding arms 210, 220 are slidably translatable with respect to one another along the longitudinal axis and the second and third sliding arms 220, 230 are slidably translatable with respect to one another along the longitudinal axis. The first sliding arm 210 includes a distally disposed engagement feature (not shown) that is couplable to the superior endplate engagement feature 112. The second sliding arm 220 includes a distally disposed first forked grasping member 221 that is hingedly coupled to the second sliding arm 220 via a second sliding arm hinge 222. The first forked grasping member 221 further includes a first fork arm 223 and a second fork arm 224, wherein the first fork arm 223 and the second fork arm 224 each include protrusions or other features (not shown) that are hingedly mateable with the first outer strut instrument engagement feature 141 and the second outer strut instrument engagement feature (not shown), respectively, to form a first fork arm hinge 225 and a second fork arm hinge 226, respectively. In an example, the third sliding arm 230 terminates distally in a non-hingedly coupled second forked grasping member 231. The second forked grasping member 231 further includes a second fork first arm 233 and a second fork second arm 234, wherein the second fork first arm 233 and the second fork second arm 234 each include protrusions or other features (not shown) that are hingedly mateable with the third outer strut instrument engagement feature 143 and the fourth outer strut instrument engagement feature 144, respectively, to form a second fork first arm hinge 235 and a second fork second arm hinge (not shown), respectively. Disposed through the proximal ends of the second fork first arm 233 and the second fork second arm 234 is a second forked grasping member base hinge 237 that hingedly couples to the base portion of an extending fork member (not shown) that splits into an extending fork member first arm 239 and an extending fork member second arm 240. The extending fork member first arm 239 and the extending fork member second arm 240 include protrusions or other features (not shown) that are hingedly mateable with the inferior endplate engagement feature 152 to form an extending fork member hinge 241. The extending fork member (not shown) may not include arms but, rather, can hingedly couple to the inferior endplate engagement feature 152 in any of a variety of other ways as would be apparent to one having ordinary skill in the art.

Figure 15:
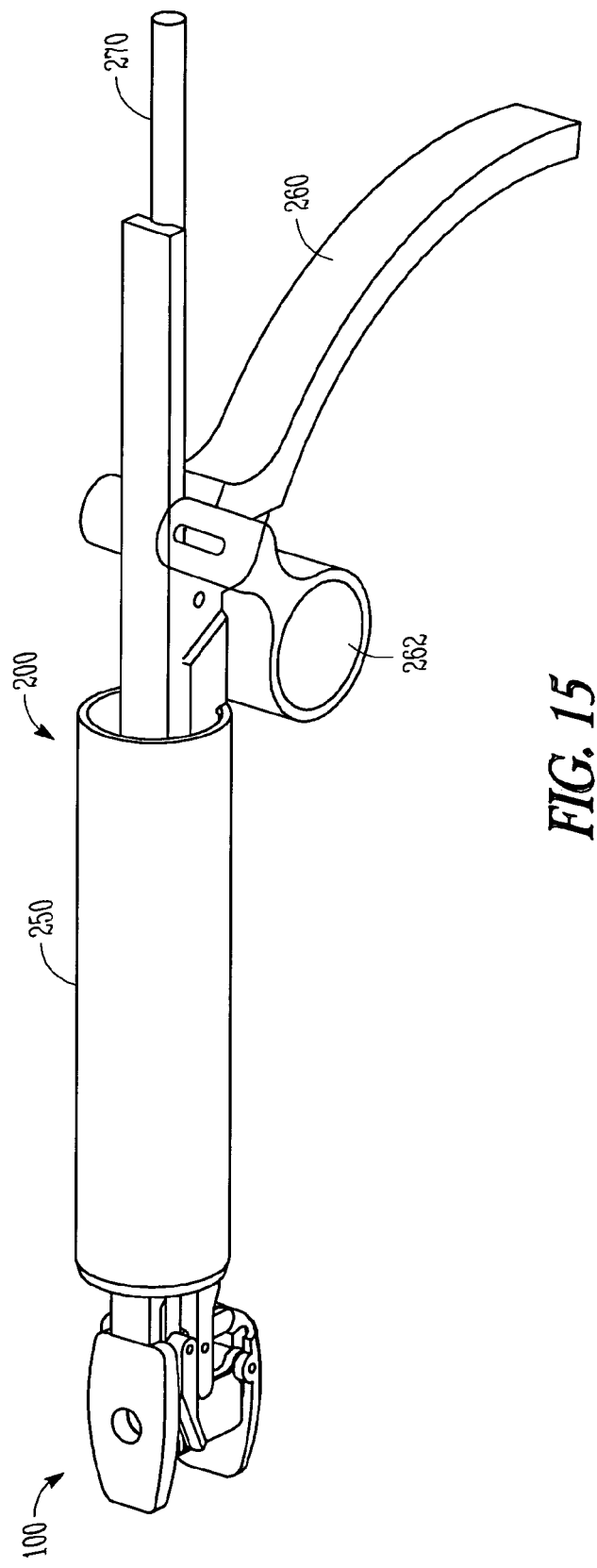
FIG. 15 is a side perspective view of an example insertion instrument coupled to the implant of FIG. 1.

The example insertion instrument 200 shown in FIG. 15 includes depictions of features, as described below, which are not shown in FIGS. 2-13, although it is contemplated that such features can be used with the insertion instrument 200 shown in FIGS. 2-13. In various examples, the insertion instrument 200 is used with a tunnel 250. The tunnel 250 is configured to be inserted within an access channel and provides space for insertion of the implant 100 and for insertion, withdrawal, and operation of the insertion instrument 200 while at the same time providing at least some protection of the body tissue in the area of the access channel from being scraped, pinched, or otherwise contacted by the implant 100 and/or the insertion instrument 200. The insertion instrument 200, in an example, includes a handle 260 and an actuator 262. In an example, the handle 260 is shaped substantially like a pistol grip and the actuator 262 is shaped substantially like a trigger. The actuator 262 is coupled to the first and second sliding arms 210, 220 to move the first and second sliding arms 210, 220, as described herein, during insertion of the implant 100. In an example, the insertion instrument 200 includes a rod 270 disposed within a channel in the insertion instrument 200 and coupled to the pinion 124 of the expansion mechanism 122. In an example, the pinion 124 is integrally attached to the rod 270. In a further example, the pinion 124 forms a distal end of the rod 270. In each of these examples, rotation of the rod 270 at the proximal end of the insertion instrument 200 rotates the pinion 124 and actuates the expansion mechanism 122 to translate the inner strut member 130 with respect to the outer strut member 140. In various examples, the rod 270 can be the shaft of a separate tool, can include an engagement feature to be matingly engaged with a separate tool, or can include a grip for manual rotation of the rod 270.

Figure 2:
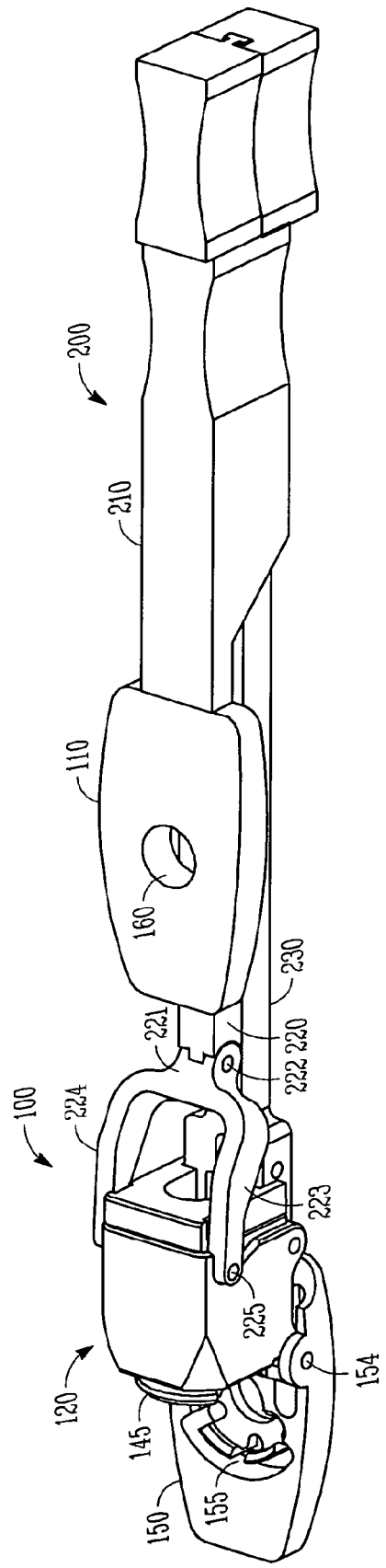
FIG. 2 illustrates a front perspective view of the implant of FIG. 1 in a non-expanded insertion profile coupled to an insertion instrument.
Figure 3:
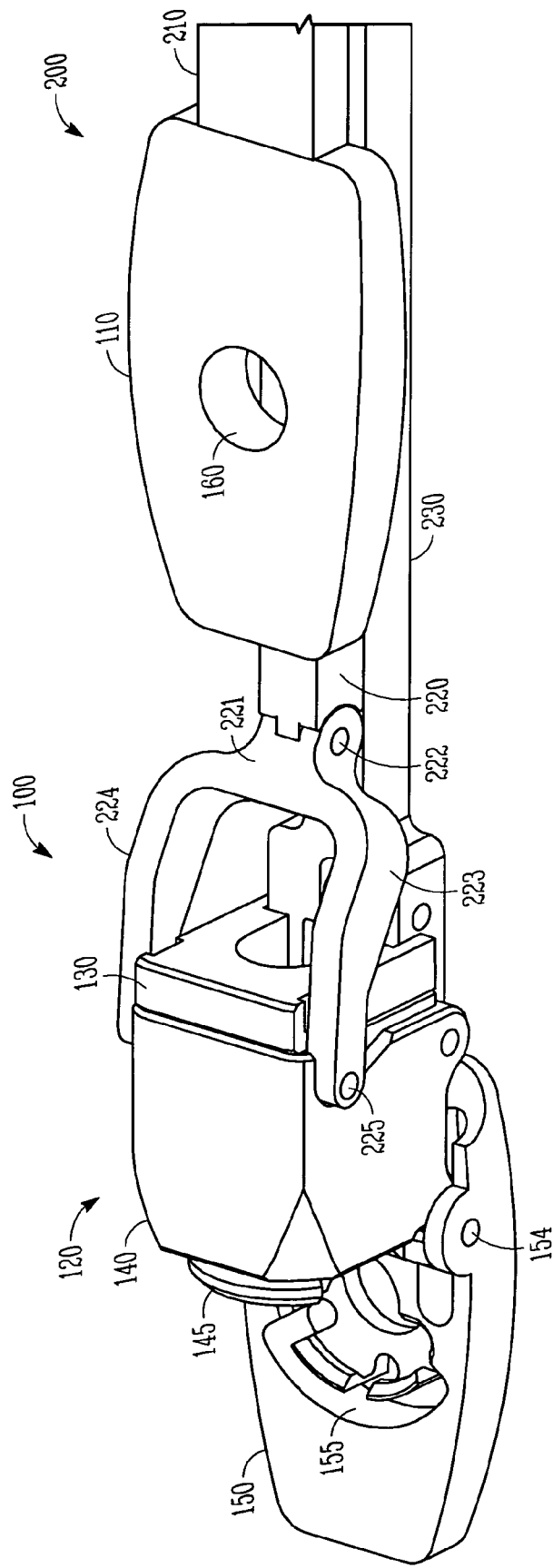
FIG. 3 is a magnified front perspective view of the implant and instrument of FIG. 2.
Figure 4:
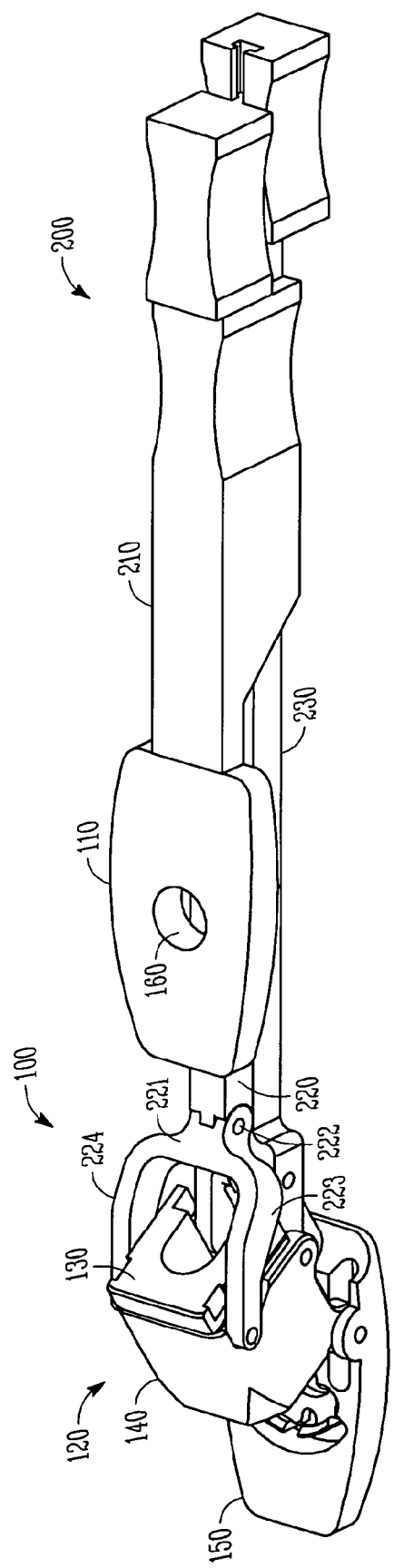
FIG. 4 illustrates a front perspective view of the implant and instrument of FIG. 2 in which the implant is in a state between the insertion configuration and the load-bearing configuration.
Figure 5:
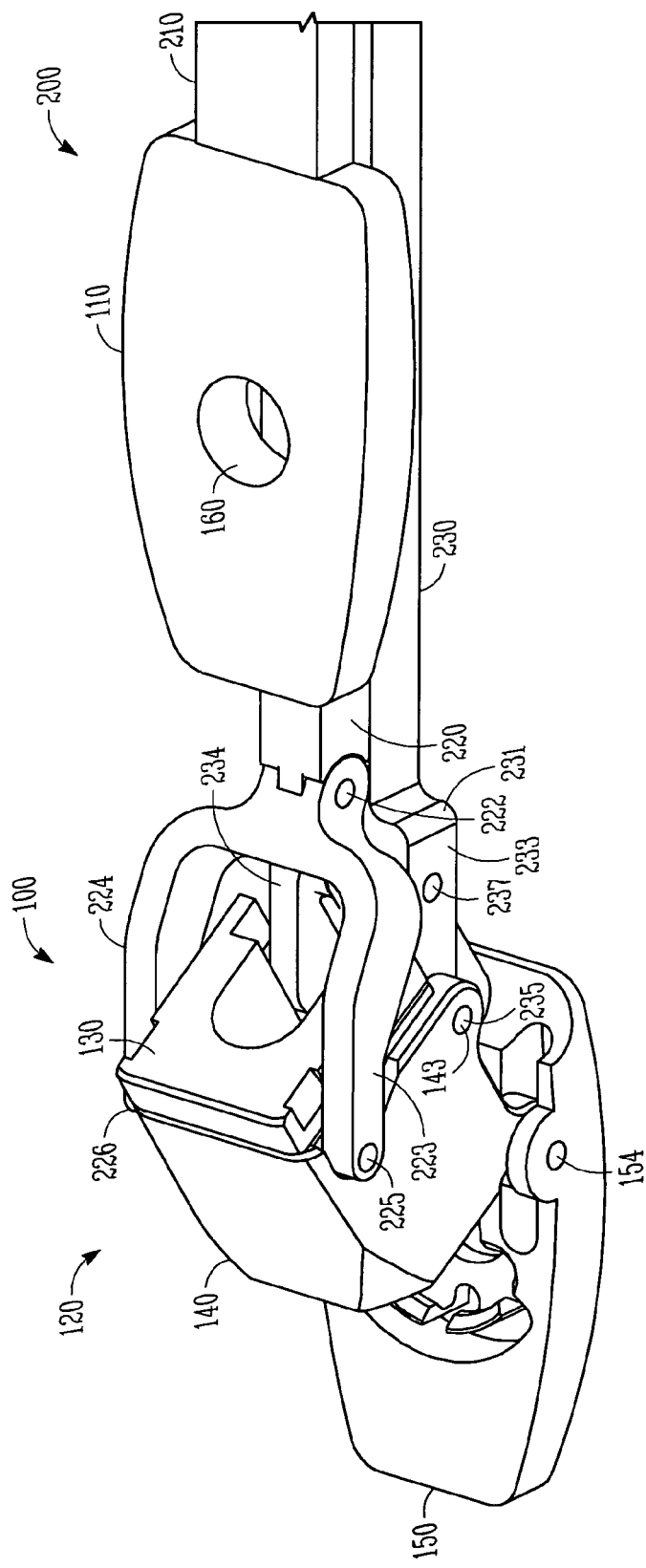
FIG. 5 is a magnified front perspective view of the implant and instrument of FIG. 4.
Figure 6:
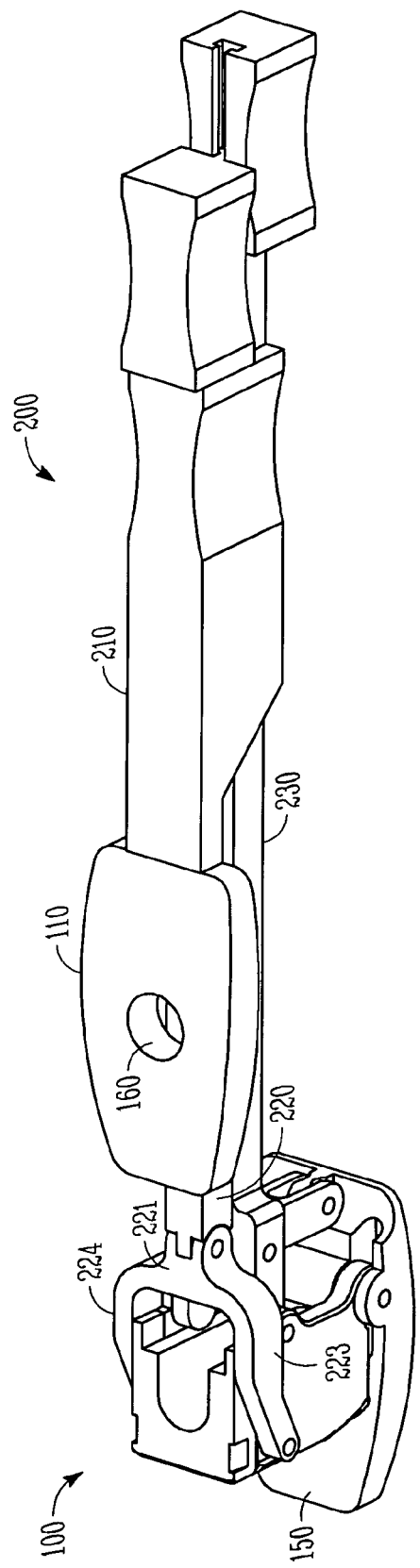
FIG. 6 illustrates a front perspective view of the implant and instrument of FIG. 2 in which the implant is in a load-bearing configuration.
Figure 7:
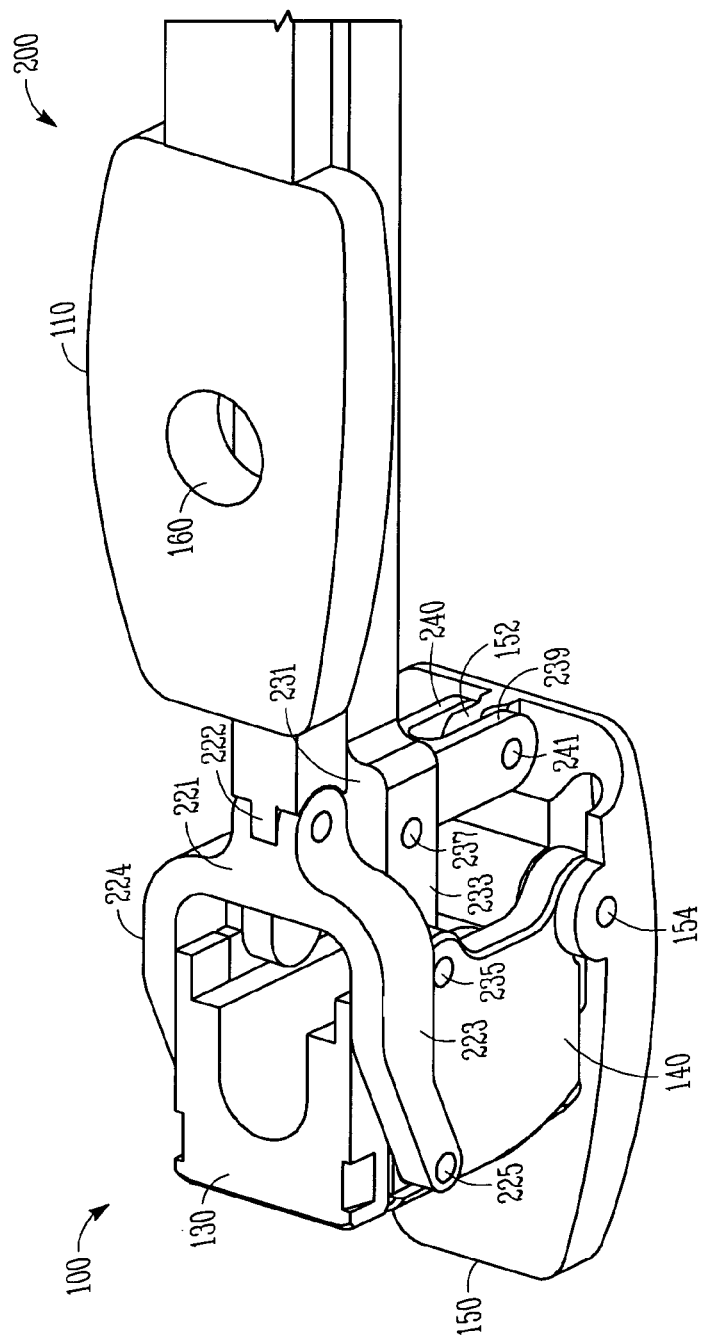
FIG. 7 is a magnified front perspective view of the implant and instrument of FIG. 6.
Figure 8:
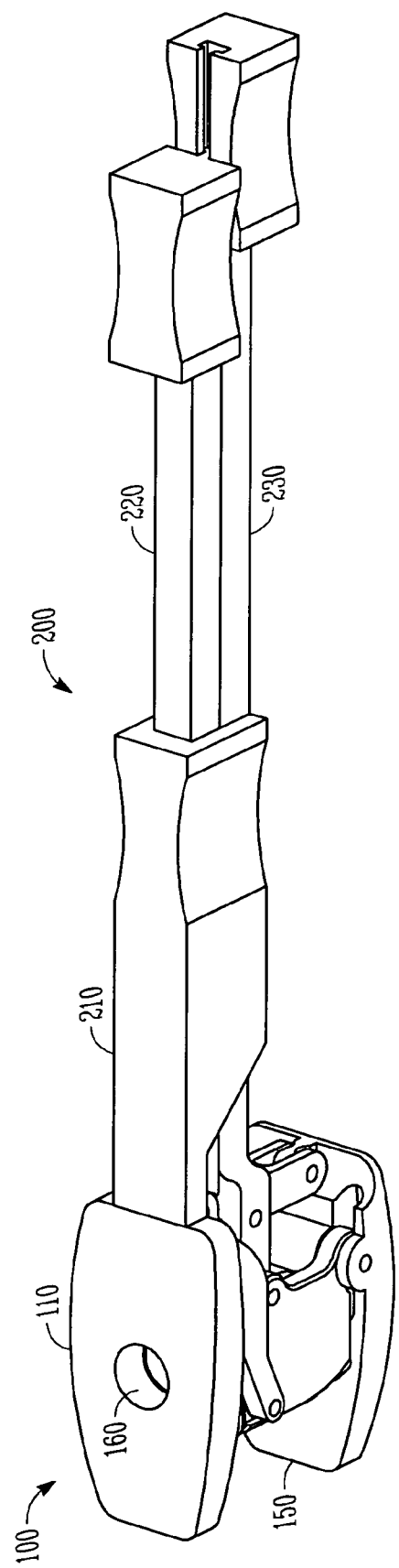
FIG. 8 illustrates a front perspective view of the implant and instrument of FIG. 2 in which the implant is in a load-bearing configuration and a superior endplate is coupled to the implant.
Figure 9:
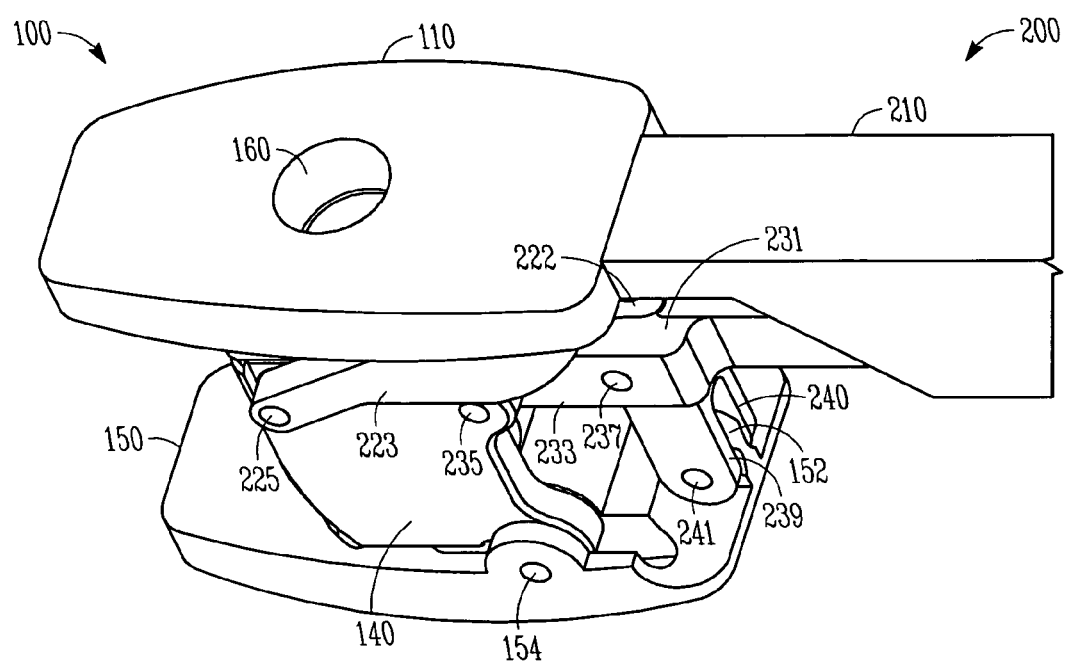
FIG. 9 is a magnified front perspective view of the implant and instrument of FIG. 8.
Figure 10:
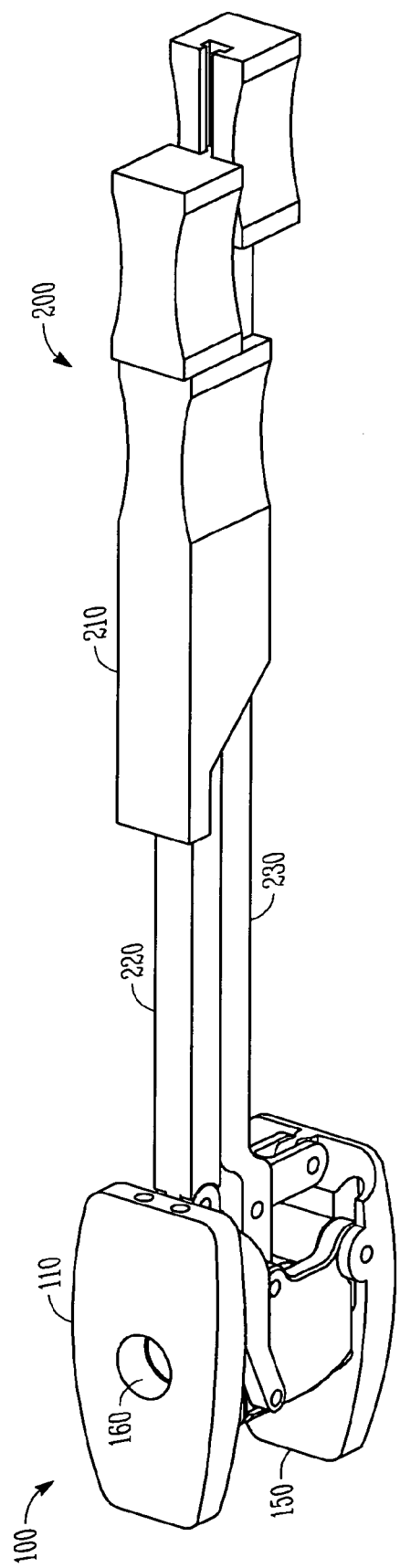
FIG. 10 illustrates a front perspective view of the implant and instrument of FIG. 2 in which the implant is in an assembled and load-bearing configuration and the superior endplate-inserter portion of the instrument is uncoupled from the superior endplate.
Figure 11:
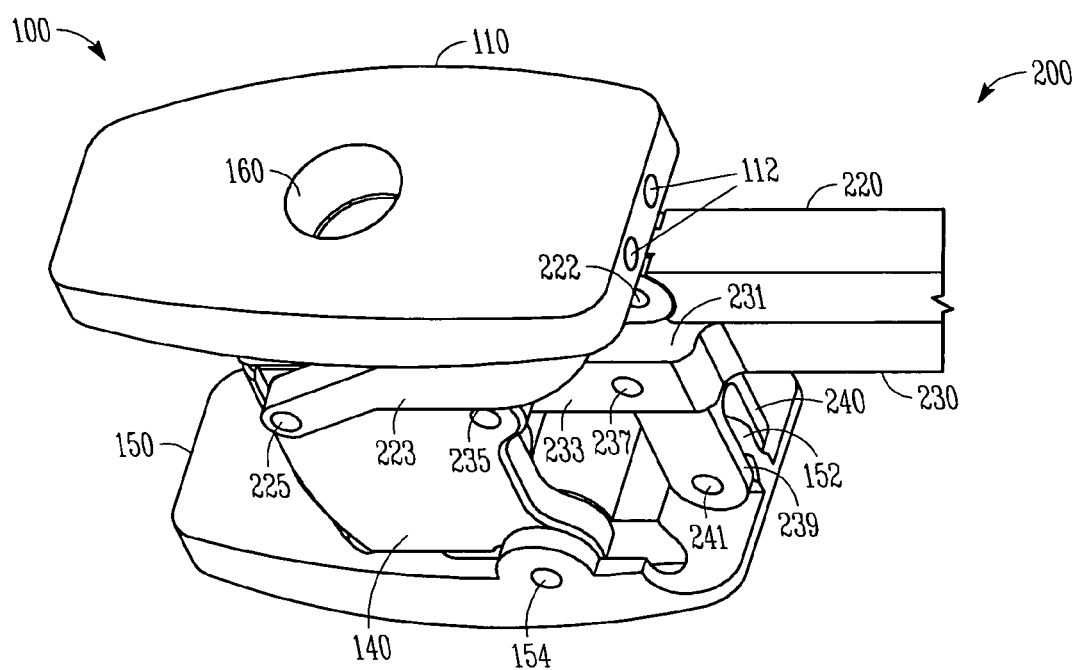
FIG. 11 is a magnified front perspective view of the implant and instrument of FIG. 10.
Figure 12:
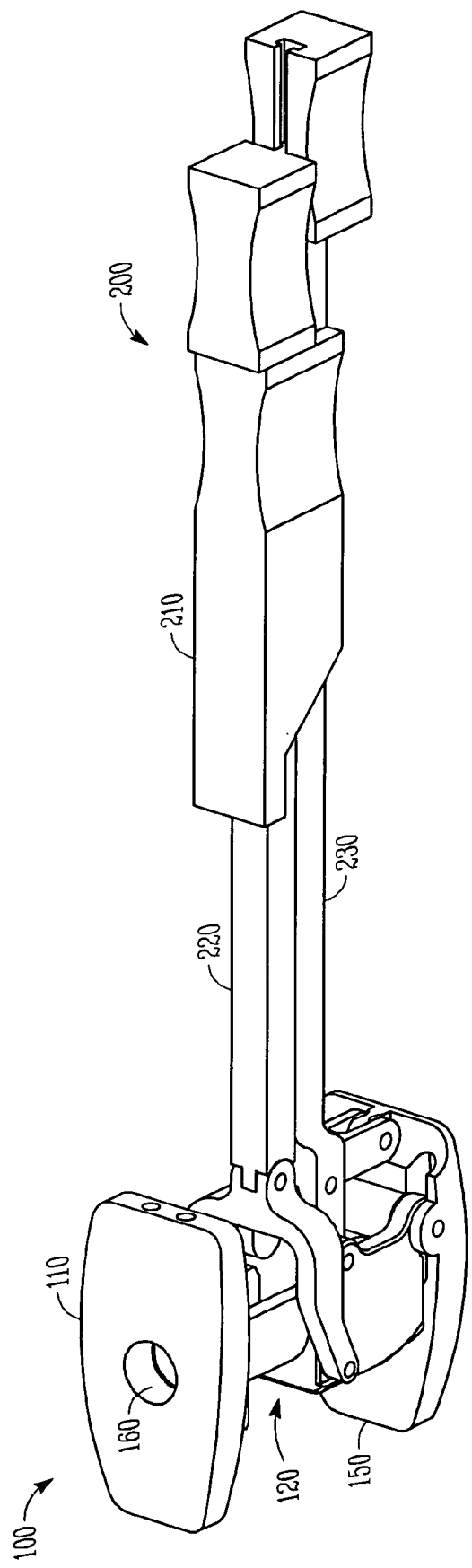
FIG. 12 illustrates a front perspective view of the implant and instrument of FIG. 2 in which the implant is in an assembled, load-bearing, and expanded configuration.
Figure 13:
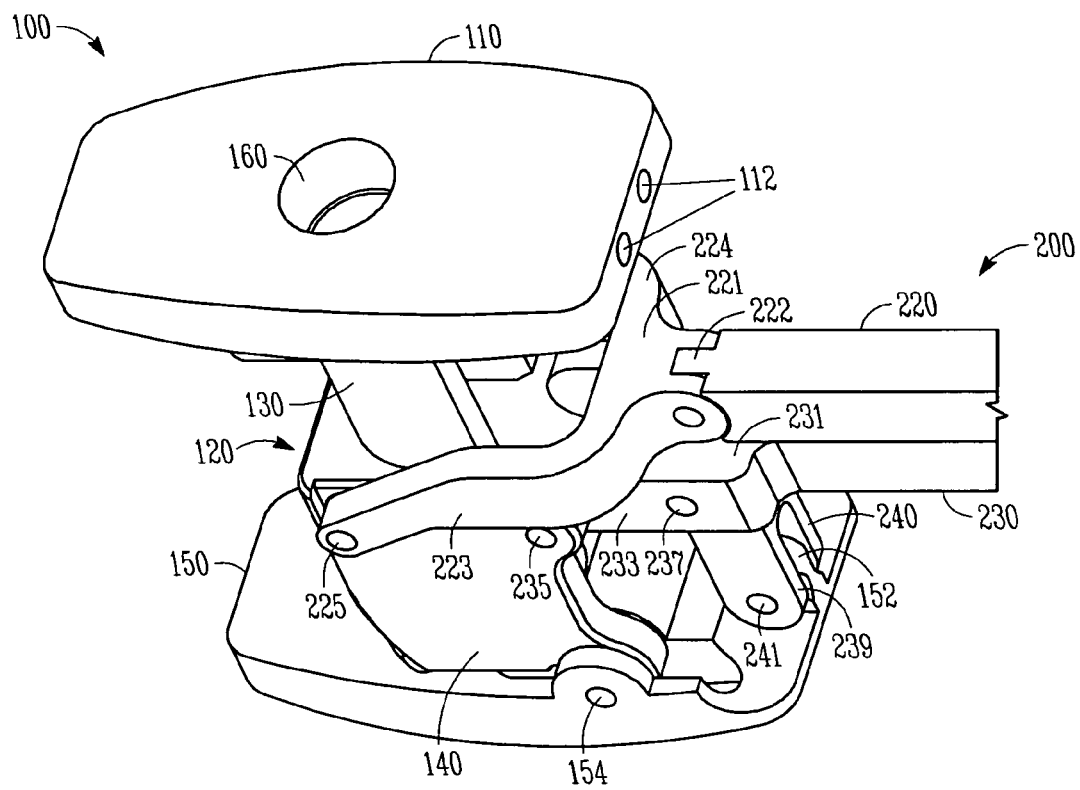
FIG. 13 is a magnified front perspective view of the implant and instrument of FIG. 12.
Figure 14:
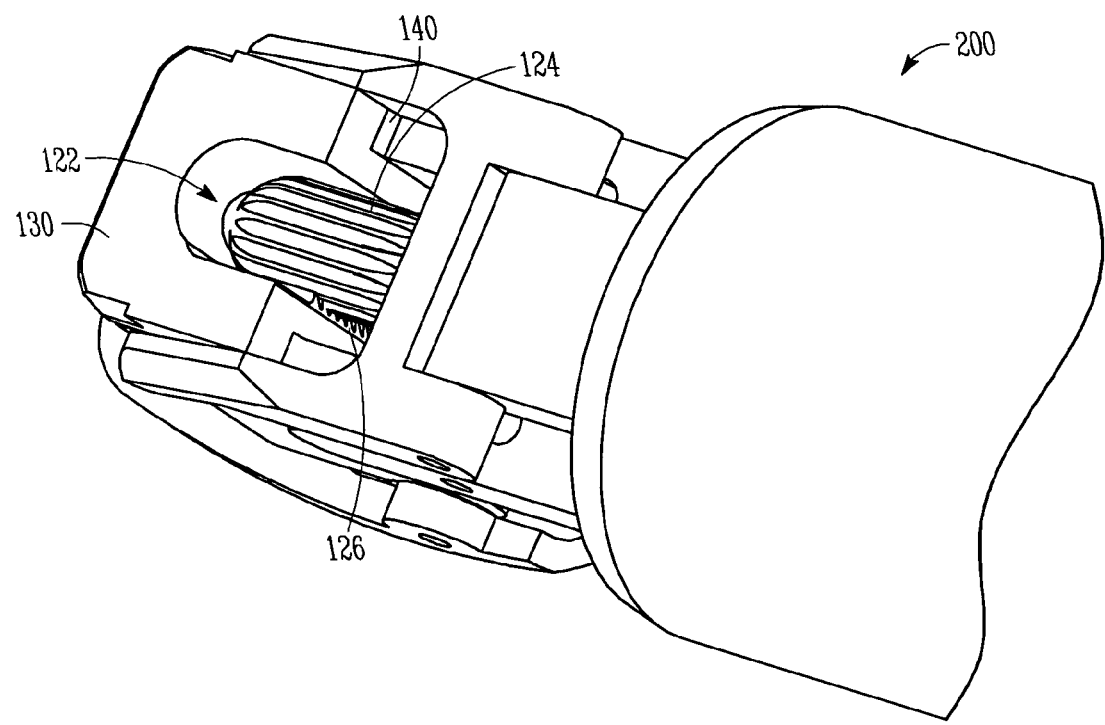
FIG. 14 is a perspective view of an example of an expansion mechanism of the implant of FIG. 1.

In operation, and in continuing reference to FIGS. 1-15, a surgeon provides an access channel to the spine and a portion of a damaged or diseased vertebral body in need of replacement is removed. The implant 100, in the insertion configuration (FIGS. 1 and 2), is engaged to the insertion instrument 200, as shown in FIGS. 2 and 3, by coupling the distal portions of the first fork arm 223 and the second fork arm 224 to the first outer strut instrument engagement feature 141 and the second outer strut instrument engagement feature 142, respectively, and by coupling the distal portions of the second fork first arm 233 and the second fork second arm 234 to the third outer strut instrument engagement feature 143 and the fourth outer strut instrument engagement feature 144, respectively, and by coupling the distal portions of the extending fork member first arm 239 and the extending fork second arm 240 to the inferior endplate engagement feature 152. The implant 100, in the insertion configuration, is then implanted into the space left by the removed portion of the diseased or damaged vertebral body by manipulating the instrument 200. Once the implant 100 is positioned with respect to the remaining vertebral bodies, the instrument 200 is manipulated to force the implant 100 into the load bearing configuration, as shown in FIGS. 4-7, by advancing the second sliding arm 220 distally with respect to the third sliding arm 230, thereby causing the second sliding arm hinge 222, the first fork arm hinge 225, the second fork arm hinge 226, the second fork first arm hinge 235, the second fork second arm hinge 236, the second forked grasping member base hinge 237, and the extending fork member hinge 241 to articulate and cause the central column 120 to rotate from the insertion configuration to the load bearing configuration and further cause the engagement of the first snap lock feature 145 with the second snap lock feature 155. As shown in FIGS. 6-9 and 15, the first sliding arm 210 is then coupled to the superior endplate 110 via the superior endplate engagement feature 112 and the first sliding arm 210 is coupled to the second sliding arm 220. The first sliding arm 210 and the distally coupled superior endplate 110 are advanced distally with respect to the second sliding arm 220, causing the superior endplate 110 to engage and couple to the superior surface of the inner strut member 130. The first sliding arm 210 is then advanced proximally with respect to the second sliding arm 220, thereby uncoupling the first sliding arm 210 from the superior endplate 110, as shown in FIGS. 10 and 11. In another example, the superior endplate 110 is pivotably coupled to the central column 120 to pivot into position with rotation of the central column 120 with respect to the inferior endplate 150, in a manner similar to that described in more detail below. The implant 100 is then expanded to a desired height, as shown in FIGS. 12 and 14, by actuating the expansion mechanism 122.

A number of different methods are envisioned as suitable for imparting force to the necessary elements to cause the inner strut member 130 to advance with respect to the outer strut member 140, depending in part upon the expansion mechanism chosen to characterize the implant 100. For example, a distracting force can be imparted to the superior and inferior endplates 110, 150 or to the inner strut member 130 by the insertion instrument 200 itself. Alternately, a separate simple expansion instrument can be coupled over the second and/or third sliding arms 220, 230 and impart the necessary force to the necessary elements of the implant 100 to cause height expansion. In addition, the separate simple expansion instrument can be coupled to the implant 100 after the instrument 200 is disengaged from the implant 100. Once the desired height has been achieved, the instrument 200 is uncoupled from the implant 100 and the access channel is sealed and the wound covered.

In an example, the implant 100 is not expandable in height via an expansion mechanism, but, rather, is simply characterized by the low profile insertion configuration and the taller load bearing configuration. In such an arrangement, the desired height of the implant can be tailored by choosing, in part, from a range of different superior endplate heights. In another example, the desired height of the implant can be tailored by choosing, in part, from a range of different strut members with varying heights.

It will be appreciated by those skilled in the art that changes could be made to the examples described above without departing from the broad inventive concept thereof. For example, the inner and outer strut members 130, 140 may be fixed in orientation relative to the superior and inferior endplates 110, 150 and expand longitudinally in a similar manner to a car jack, as opposed to expanding pivotably and longitudinally, as is described in various examples above. It is understood, therefore, that this invention is not limited to the particular examples disclosed, but it is intended to cover modifications within the spirit and scope of the present invention as defined by the present description.

Referring now to FIGS. 16A-D, in another example, a low insertion-profile VBR implant 300 is shown. An associated insertion device, although not shown for ease of illustration, is used with the implant 300 and is substantially similar to the insertion device 200 described above. In an example, the insertion device used with the implant 300 differs from the insertion device 200 described above in that it lacks the structure required to slide the superior endplate into position, for reasons that should become apparent from the description of the implant 300 below. It is noted that, in various examples, in addition to the features and properties described below, the implant 300 can include one or more features and/or one or more properties similar to those included with the implant examples discussed above.

Figure 16A:
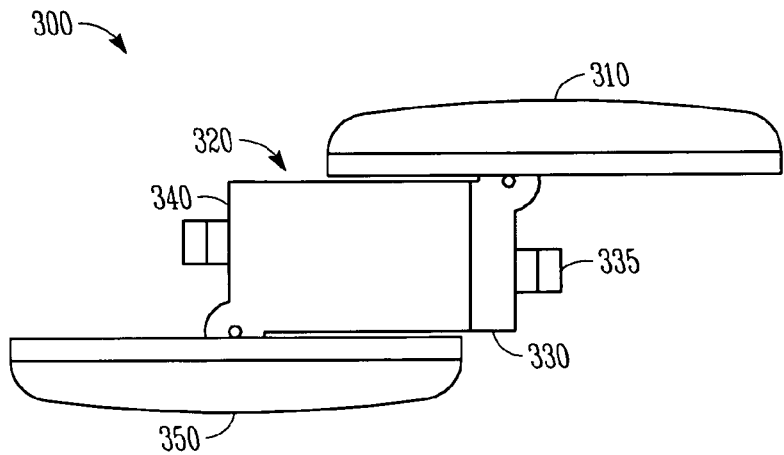
FIGS. 16A-D are elevational views of a low insertion profile vertebral body replacement implant in accordance with an example of the present invention.
Figure 16B:
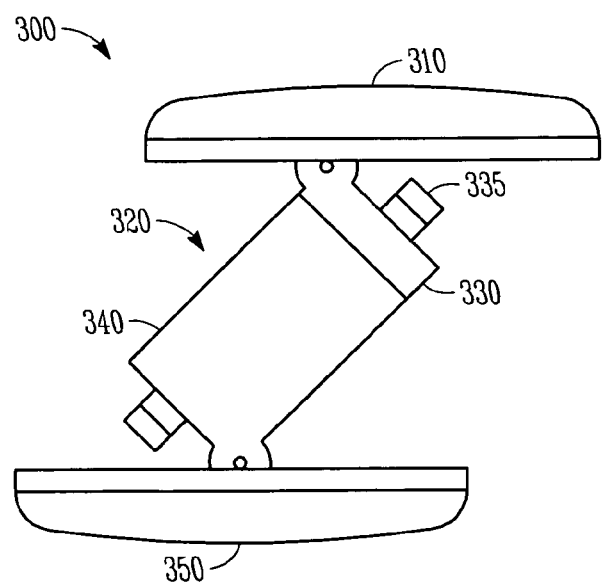
Figure 16C:
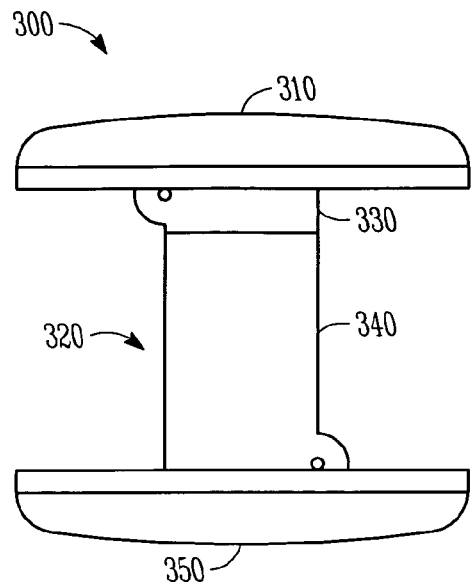
Figure 16D:
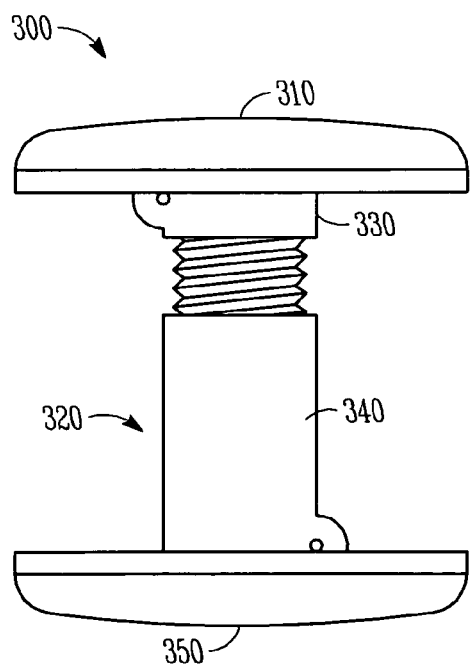

The implant 300, in an example, includes an inferior endplate 350. A central column 320 is pivotably coupled to the inferior endplate 350. In an example, the central column 320 includes an inner strut member 330 telescopically coupled with an outer strut member 340. In a further example, the inner strut member 330 is telescopically disposed within the outer strut member 340. As shown in FIG. 16D, the inner strut member 330 and the outer strut member 340, in an example, are telescopically expandable in height with respect to one another to provide a low insertion height/profile and permit expansion into a final expanded configuration between vertebral bodies. In various examples, the inner strut member 330 is translatable with respect to the outer strut member 340 to thereby provide height expansion to the central column 320 via the inclusion of an expansion mechanism. In various examples, the expansion mechanism includes a ratcheting expansion mechanism, a threaded expansion mechanism, a rack and pinion expansion mechanism, a stacking shim expansion mechanism, or other expansion mechanism.

In the example shown in FIGS. 16A-D, the implant 300 includes a superior endplate 310 pivotably engaged with the central column 320. In an example, the inner strut member 330 includes a first snap lock feature 335 that is configured to mate with a corresponding second snap-lock feature on the inferior surface of the superior endplate 310 to retain the superior endplate 310 securely in a load bearing configuration with respect to the central column 320.

In operation, in an example, the implant 300 is inserted similarly to the insertion of the implant 100 described above. However, the superior endplate 310 pivots into place with the pivoting of the central column 320. In an example, the insertion device is configured to pivot the superior endplate 310 into position. In another example, the superior endplate 310 is pivoted into place with the pivoting of the central column 320 and sliding contact of the superior endplate 310 with an inferior endplate of a superior vertebral body against which the superior endplate 310 is intended to bear in the load bearing configuration.

Figure 17A:
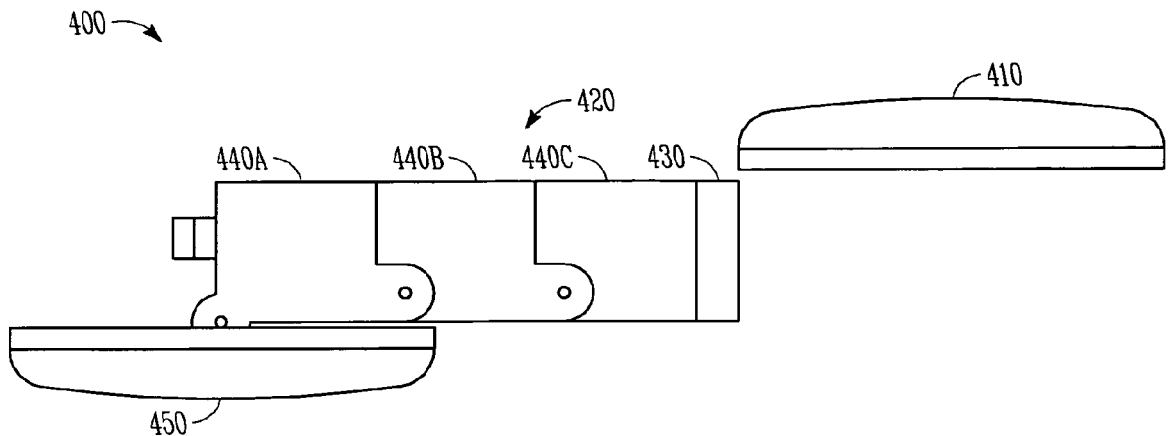
FIGS. 17A-C are elevational views of a low insertion profile vertebral body replacement implant in accordance with an example of the present invention.
Figure 17B:
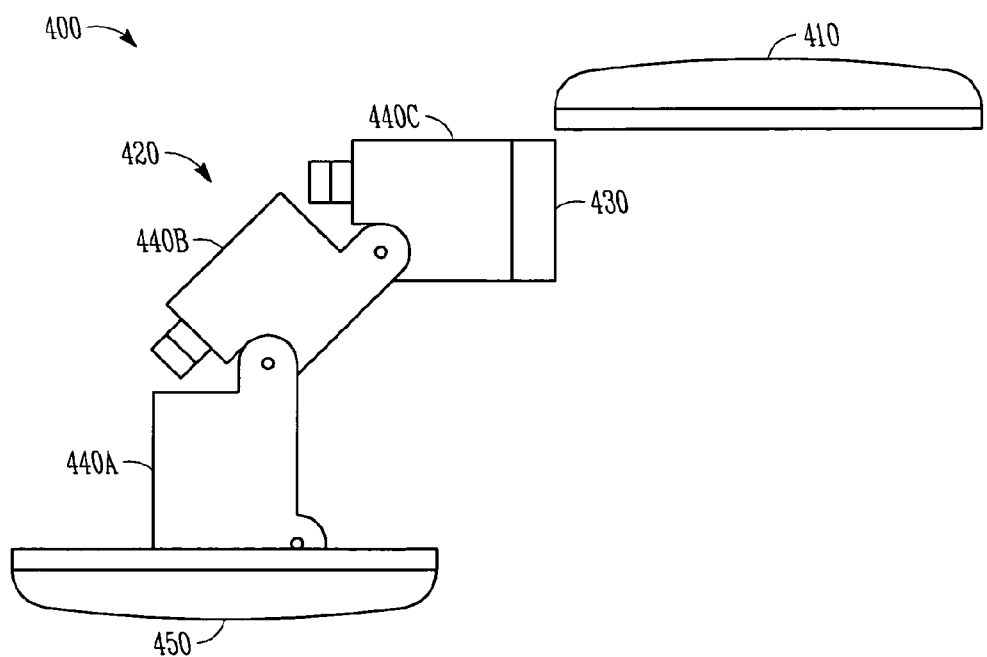
Figure 17C:
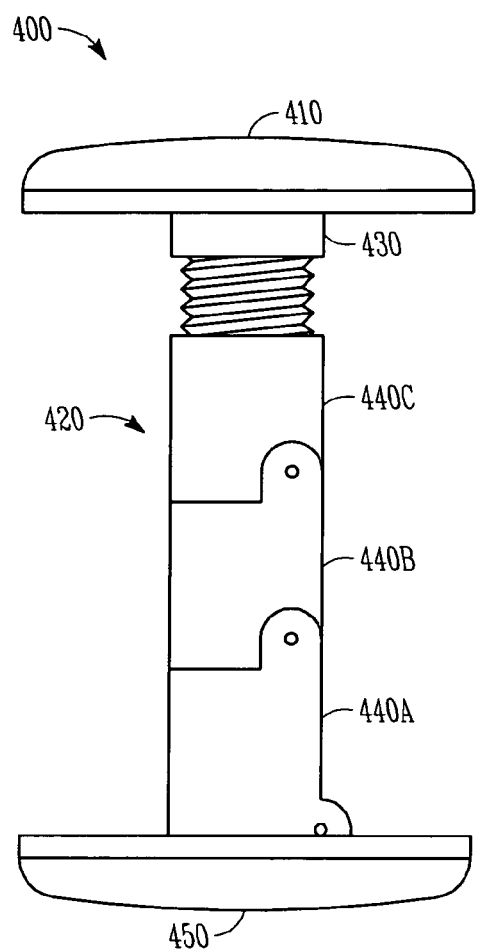

Referring now to FIGS. 17A-C, in another example, a low insertion-profile VBR implant 400 is shown. An associated insertion device, although not shown for ease of illustration, is used with the implant 400 and is substantially similar to the insertion device 200 described above. It is noted that, in various examples, in addition to the features and properties described below, the implant 400 can include one or more features and/or one or more properties similar to those included with the implant examples discussed above.

The implant 400, in an example, includes an inferior endplate 450. A central column 420 is pivotably coupled to the inferior endplate 450. In an example, the central column 420 includes two or more pivoting segments. In the example shown in FIGS. 17A-C, the central column 420 includes first, second, and third pivoting segments 440A, 440B, 440C, with the first pivoting segment 440A pivotably coupled to the inferior endplate 450, the second pivoting segment 440B pivotably coupled to the first pivoting segment 440A, and the third pivoting segment 440C pivotably coupled to the second pivoting segment 440B. The implant 400 includes an inner strut member 430 telescopically coupled with the third pivoting segment 440C. In a further example, the inner strut member 430 is telescopically disposed within the third pivoting segment 440C. As shown in FIG. 17C, the inner strut member 430 and the third pivoting segment 440C, in an example, are telescopically expandable in height with respect to one another to provide a low insertion height/profile and permit expansion into a final expanded configuration between vertebral bodies. In various examples, the inner strut member 430 is translatable with respect to the third pivoting segment 440C to thereby provide height expansion to the central column 420 via the inclusion of an expansion mechanism. In various examples, the expansion mechanism includes a ratcheting expansion mechanism, a threaded expansion mechanism, a rack and pinion expansion mechanism, a stacking shim expansion mechanism, or other expansion mechanism. Although shown with three pivotable segments 440A, 440B, 440C, in various examples, the implant can include more or fewer than three segments, depending upon the final desired height of the implant, the size of the access channel, etc. In some examples, the segments of the implant can be preassembled. In other examples, the segments of the implant can be assembled at the time of surgery to enable customization of the implant, for instance, based on the location for the implant, the size and shape of the access channel, and various other conditions present at the time of surgery.

In the example shown in FIGS. 17A-C, the implant 400 includes a superior endplate 410 slidably engageable with the central column 420 in a manner similar to that described above with respect to the implant 100. In other examples, the superior endplate 410 is pivotably engaged with the central column 420 in a manner similar to that described above with respect to the implant 300.

In operation, in an example, the implant 400 is inserted similarly to the insertion of the implant 100 described above. However, in an example, the associated insertion device is configured to pivot all of the segments of the central column 420 into a substantially aligned load-bearing position, as shown in FIG. 17C. Once the central column 420 is pivoted into the load-bearing position and the superior endplate 410 is slid or pivoted into position on the central column 420, the expansion mechanism can be actuated to increase the height of the central column 420 to a desired final height to bear against an inferior endplate of a superior vertebral body against which the superior endplate 410 is intended to bear in the load bearing configuration.

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to allow the reader to quickly ascertain the nature of the technical disclosure. It is submitted with the understanding that it will not be used to interpret or limit the scope or meaning of the claims.

What is claimed is:

1. A system comprising:
   an implantable device configured to be inserted between a first vertebral body and a second vertebral body, the implantable device including:
   a first endplate having a first surface and a second surface, the second surface configured to face an endplate of the first vertebral body;
   a central member including a first portion and a second portion that is spaced from the first portion, wherein the first portion is pivotably coupled to the first endplate so as to move the second portion with respect to the first endplate, the central member further including an outer strut member and an inner strut member that is telescopically movable with respect to the outer strut member; and
   a second endplate having a first surface and a second surface, the first surface of the second endplate configured to face an endplate of the second vertebral body, the second endplate configured to engage with the central member such that the central member is disposed between the first and second endplates;
   wherein the implantable device is movable from a first insertion configuration to a second load-bearing configuration, such that 1) in the first insertion configuration the second portion is spaced from the first endplate, 2) when moving from the first insertion configuration to the second load-bearing configuration, the central member pivots with respect to the first endplate along a direction that moves the second portion toward the first endplate and 3) in the second load-bearing configuration the second portion is supported by the first endplate such that the central member is prevented from further pivoting in the direction; and
   an insertion instrument removably couplable to the implantable device, the insertion instrument configured to advance the implantable device in the first insertion configuration in between the first vertebral body and the second vertebral body, the insertion instrument being actuatable to place the implantable device in the second load-bearing configuration by pivoting the central member with respect to at least one of the first endplate and the second endplate.

2. The system of claim 1, wherein the central member is pivotable through substantially ninety degrees with respect to the first endplate.

3. The system of claim 1, wherein a height of the implantable device in the first insertion configuration is less than a height of the implantable device in the second load-bearing configuration.

4. The system of claim 1, wherein the implantable device further comprises an expansion mechanism configured to telescopically move the inner strut member with respect to the outer strut member.

5. The system of claim 4, wherein the expansion mechanism includes a rack and pinion.

6. The system of claim 1, wherein the insertion instrument is couplable to the second endplate, the insertion instrument being configured to slidingly advance the second endplate into engagement with the second coupling feature of the central member.

7. The system of claim 1, wherein the central member includes at least first and second pivoting segments, the first pivoting segment being pivotable with respect to the first endplate, and the second pivoting segment being pivotable with respect to the first pivoting segment.

8. The system of claim 1, wherein the central member is lockable in a pivoted position, the central member being in the pivoted position with the implantable device in the second load-bearing configuration.

9. The system of claim 1, wherein the first endplate includes a first coupling feature, the central member includes a second coupling feature configured to engage with the first coupling feature such that the central member is pivotable with respect to the first endplate about a pivot axis that passes through both the first and second coupling features, the central member further includes a third coupling feature, and the second endplate includes a fourth coupling feature, such that the third and fourth coupling features are configured to engage when the implantable device is in the second load-bearing configuration.

10. The system of claim 9, wherein the fourth coupling feature is configured to slidingly engage with the third coupling feature of the central member.

11. The system of claim 9, wherein the fourth coupling feature of the second endplate is pivotably engaged with the third coupling feature of the central member.

12. The system of claim 9, wherein the insertion instrument includes a first sliding arm and a second sliding arm, wherein the second sliding arm is configured to slide to pivot the central member with respect to the first endplate, and the first sliding arm is configured to slide to engage the third coupling feature of the central member with the fourth coupling feature of the second endplate.

13. The system of claim 12, wherein the insertion instrument includes a third sliding arm, wherein the second sliding arm is slidable with respect to the third sliding arm to pivot the central member with respect to the first endplate, and the first sliding arm is slidable with respect to the second sliding arm to engage the third coupling feature of the central member with the fourth coupling feature of the second endplate.

14. The system of claim 1, wherein the first surface of the first and second endplates is a superior surface, the second surface of the first and second endplates is an inferior surface, the inferior surface of the first endplate is configured to face a superior endplate of the first vertebral body; and the superior surface of the second endplate is configured to face an inferior endplate of the second vertebral body.

15. The system of claim 14, wherein the central member is pivotably coupled proximate a proximal side of the superior surface of the first endplate.

16. The system of claim 1, wherein the second portion includes a locking feature that is configured to mate with a corresponding locking feature of the first endplate.

17. An implantable device configured to be inserted in an insertion direction between a first vertebral body and a second vertebral body, the implantable device comprising:
   a distal end and a proximal end, the distal end spaced from the proximal end in the insertion direction;
   a first endplate having a first surface and a second surface, the second surface configured to contact an endplate of the first vertebral body, the first endplate including a first coupling feature;
   a central member including an outer strut member, an inner strut member telescopically movable with respect to the outer strut member, and a second coupling feature configured to engage with the first coupling feature so as to pivotably couple the central member to the first endplate, the central member further including a third coupling feature; and
   a second endplate having a first surface and a second surface, the first surface of the second endplate configured to contact an endplate of the second vertebral body, the second endplate including a fourth coupling feature configured to engage with the third coupling feature of the central member, wherein the implantable device includes a first insertion configuration and a second load-bearing configuration such that when the implantable device is in the first insertion configuration, the central member is at a first angular position with respect to the first endplate such that the second coupling feature is located closer to the distal end of the device than the third coupling feature, and when the implantable device is in the second load-bearing configuration: 1) the central member is at a second angular position with respect to the first endplate that is different than the first angular position such that at least a portion of the third coupling feature is located closer to the distal end of the device than the second coupling feature; and 2) the fourth coupling feature is slidable with respect to the third coupling feature.

18. The implantable device of claim 17, wherein the central member is pivotable from the first angular position through substantially ninety degrees with respect to the first endplate to the second angular position.

19. The implantable device of claim 17, wherein a height of the implantable device in the first insertion configuration is less than a height of the implantable device in the second load-bearing configuration.

20. The implantable device of claim 17, comprising an expansion mechanism configured to telescopically move the inner strut member with respect to the outer strut member.

21. The implantable device of claim 17, wherein the central member includes at least first and second pivoting segments, the first pivoting segment being pivotable with respect to the first endplate, and the second pivoting segment being pivotable with respect to the first pivoting segment.

22. The implantable device of claim 17, wherein the central member is lockable in the second angular position, the central member being in the second angular position with the implantable device in the second load-bearing configuration.

23. The implantable device of claim 17, wherein the first surface of the first and second endplates is a superior surface, the second surface of the first and second endplates is an inferior surface, the inferior surface of the first endplate is configured to face a superior endplate of the first vertebral body; and the superior surface of the second endplate is configured to face an inferior endplate of the second vertebral body.

24. The implantable device of claim 23, wherein the implantable device is configured to detachably engage with an insertion instrument, the insertion instrument configured to advance the implantable device in the first insertion configuration in between the superior endplate of the first vertebral body and the inferior endplate of the second vertebral body, the insertion instrument being actuatable to place the implantable device in the second load-bearing configuration.

25. The implantable device of claim 23, wherein the fourth coupling feature of the second endplate is pivotably engaged with the third coupling feature of the central member.

26. The implantable device of claim 17, wherein the central member includes a central member surface that extends away from the second coupling feature such that the central member surface defines a length, the first insertion configuration includes the central member at a first angular position with respect to the first endplate such that the central member surface extends away from the first surface of the first endplate in a vertical direction, and the second load-bearing configuration includes the central member at a second angular position with respect to the first endplate such that the central member surface faces the first surface of the first endplate such that the central member surface is adjacent to the first surface of the first endplate along the length of the central member surface.

27. A method comprising:
   placing an implantable device between a first vertebral body and a second vertebral body, the implantable device including a first endplate, a second endplate, and a central member, the central member including a first portion and a second portion spaced from the first portion;
   pivoting the central member of the implantable device in a rotational direction about a pivot axis that passes through the first portion from a first angular position with respect to the first endplate to a second angular position with respect to the first endplate, such that in the first angular position the second portion is spaced from the first endplate and in the second angular position the second portion is supported by the first endplate such that the central member is blocked from pivoting in the first direction about the pivot axis with respect to the first endplate; and
   separate from the pivoting step, translating the second endplate of the implantable device relative to the first endplate along a translational direction such that the central member is disposed between the first and second endplates to place the implantable device in a load-bearing configuration.

28. The method of claim 27, wherein the pivoting step includes pivoting the central member substantially ninety degrees about the pivot axis from the first angular position with respect to the first endplate of the implantable device to the second angular position with respect to the first endplate.

29. The method of claim 27, further comprising the step of attaching the implantable device to an insertion instrument, and wherein the pivoting step includes actuating the insertion instrument to pivot the central member.

30. The method of claim 29, wherein the actuating step includes sliding one sliding arm of the insertion instrument with respect to another sliding arm of the insertion instrument.

31. The method of claim 29, further comprising the step of removing the insertion instrument from engagement with the implantable device.

32. The method of claim 27, wherein the moving step includes actuating the insertion instrument to move the second endplate into engagement with the central member.

33. The method of claim 32, wherein the actuating step includes sliding one sliding arm of the insertion instrument with respect to another sliding arm of the insertion instrument.

34. The method of claim 27, wherein the moving step includes pivoting the second endplate with respect to the central member.

35. The method of claim 27, wherein the pivoting step includes locking the central member in the second angular position.

36. The method of claim 27, further comprising the step of expanding the implantable device to increase a height of the implantable device, measured from the first endplate to the second endplate.

37. The method of claim 36, wherein the expanding step includes actuating an expansion mechanism to telescopically move an inner strut member of the central member with respect to an outer strut member of the central member.

38. The method of claim 27, wherein the translating step is performed after completion of the pivoting step.

\* \* \* \* \*